United States Patent [19]

Imran

[11] Patent Number: 5,342,295
[45] Date of Patent: Aug. 30, 1994

[54] CATHETER ASSEMBLY, CATHETER AND MULTI-PORT INTRODUCER FOR USE THEREWITH

[75] Inventor: Mir A. Imran, Palo Alto, Calif.

[73] Assignee: Cardiac Pathways Corporation, Sunnyvale, Calif.

[21] Appl. No.: 126,314

[22] Filed: Sep. 24, 1993

[51] Int. Cl.$^5$ .............. A61M 3/00; A61M 31/00; A61M 5/178; A61M 5/00
[52] U.S. Cl. .............................. 604/43; 604/53; 604/164; 604/264
[58] Field of Search ................... 604/43–45, 604/53, 164, 170, 94, 264, 280, 284; 128/656–658

[56] References Cited

U.S. PATENT DOCUMENTS

| | | | |
|---|---|---|---|
| 4,637,388 | 1/1987 | Melady | 128/207.14 |
| 4,670,009 | 6/1987 | Bullock | 604/280 |
| 4,671,291 | 6/1987 | Wilson | 128/658 |
| 4,769,005 | 9/1988 | Ginsburg et al. | 604/53 |
| 4,838,879 | 6/1989 | Tanabe et al. | 604/280 |
| 4,905,667 | 3/1990 | Foerster et al. | 128/4 |
| 4,920,980 | 5/1990 | Jackowski | 128/786 |
| 4,963,128 | 10/1990 | Daniel et al. | 600/7 |
| 5,078,714 | 1/1992 | Katims | 606/38 |
| 5,135,599 | 8/1992 | Martin et al. | 156/294 |
| 5,149,330 | 9/1992 | Brightbill | 604/280 |
| 5,203,338 | 4/1993 | Jang | 128/662.06 |
| 5,211,176 | 5/1993 | Ishiguro et al. | |
| 5,215,527 | 6/1993 | Beck et al. | 604/164 |
| 5,236,417 | 8/1993 | Wallis | 604/82 |

FOREIGN PATENT DOCUMENTS 2565491 12/1985 France ................. 604/284

*Primary Examiner*—John D. Yasko
*Assistant Examiner*—Adam J. Cermak
*Attorney, Agent, or Firm*—Flehr, Hohbach, Test, Albritton & Herbert

[57] ABSTRACT

Catheter assembly for use in performing medical procedures in the body of a patient having a vessel therein comprising a multi-port introducer adapted to be inserted into a vessel of the patient and a plurality of catheters disposed in the multi-port introducer and adapted to be disposed in the vessel of the patient.

16 Claims, 2 Drawing Sheets

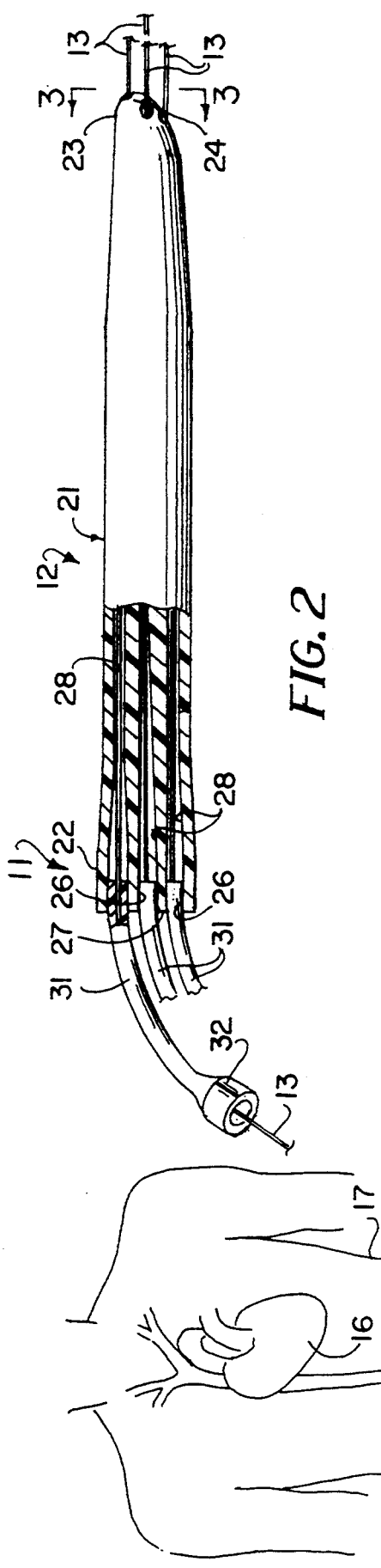
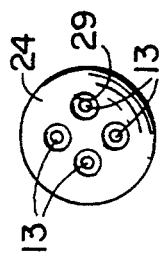
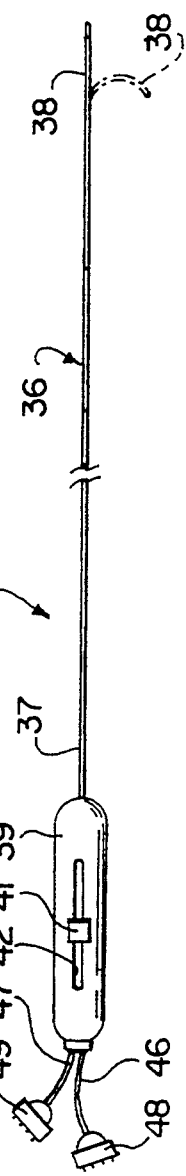
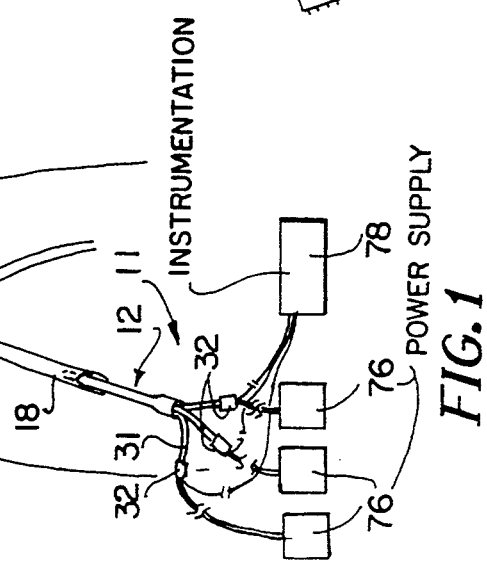

CATHETER ASSEMBLY, CATHETER AND MULTI-PORT INTRODUCER FOR USE THEREWITH

This invention relates to a catheter assembly, catheter and multi-port introducer for use therewith and more particularly to a diagnostic catheter assembly for electrophysiology studies and diagnostic catheter and multi-port introducer for use therewith.

Heretofore electrophysiology diagnostic studies have been carried out in cath labs for the purpose of studying the electrical characteristics of the heart. Typically this is accomplished with diagnostic catheters of various configurations of electrodes at the distal extremities. These catheters are 6 or 7 French in size and during an electrophysiology study three to four of such catheters are utilized and sometimes a maximum of five. These catheters are positioned inside the heart in various locations. To accomplish such studies, a physician typically has to make several incisions and utilize several introducers with hemostasis valves on the proximal ends of the same. When such catheters and introducers are removed, there remains four or five holes in the veins or artery of the patient which may cause major problems for the patients, as for example hematomas. Persistent bleeding is a problem because typically such patients have been heparinized. Thus it is often necessary to hold down physically the puncture sites for periods as great as 20 minutes before clotting occurs. There is therefore need for new and improved catheter and introducer for the same and a method which will greatly reduce the number of puncture sites to only one.

In general, it is an object of the present invention to provide a catheter assembly, catheter and multi-port introducer for use therewith so that only a single site is required.

Another object of the invention is to provide a catheter assembly, catheter, multi-port introducer and method which is particularly useful for making diagnostic electrophysiology studies.

Another object of the invention is to provide a catheter assembly of the above character which utilizes a plurality of small diameter catheters which are introduced through a single multi-port introducer.

Another object of the invention is to provide catheters of the above character which are small in size and which can be provided in different electrode configurations.

Another object of the invention is to provide a catheter of the above character in which the distal extremity can be steered.

Another object of the invention is to provide a multi-lumen introducer of the above character which can receive a plurality of catheters through its multi-ports.

Another object of the invention is to provide a catheter of the above character which has a distal extremity which is very flexible to ensure that it will not penetrate the endocardium of the heart.

Another object of the invention is to provide a catheter of the above character in which the distal extremity and proximal extremities of the catheters are marked so that one catheter can be distinguished from another.

Another object of the invention is to provide a multi-port introducer of the above character which can be relatively short and which is provided with an atraumatic distal extremity.

Another object of the invention is to provide a multi-port introducer of the above character which is relatively long and which has an atraumatic distal extremity so that it can be introduced into a vessel of the patient adjacent the heart.

Additional objects and features of the invention will appear from the following description which the preferred embodiments are set forth in detail in conjunction with the accompanying drawings.

FIG. 1 is a schematic illustration showing the manner in which the catheter assembly for the present invention can be introduced into the femoral vein and into the heart of the patient.

FIG. 2 is a side elevational view partially in cross section of the multi-port introducer of the assembly shown in FIG. 1.

FIG. 3 is an end elevational view taken along the line 3—3 of FIG. 2.

FIG. 4 is a side elevational view of a catheter incorporating the present invention.

Figure 5:
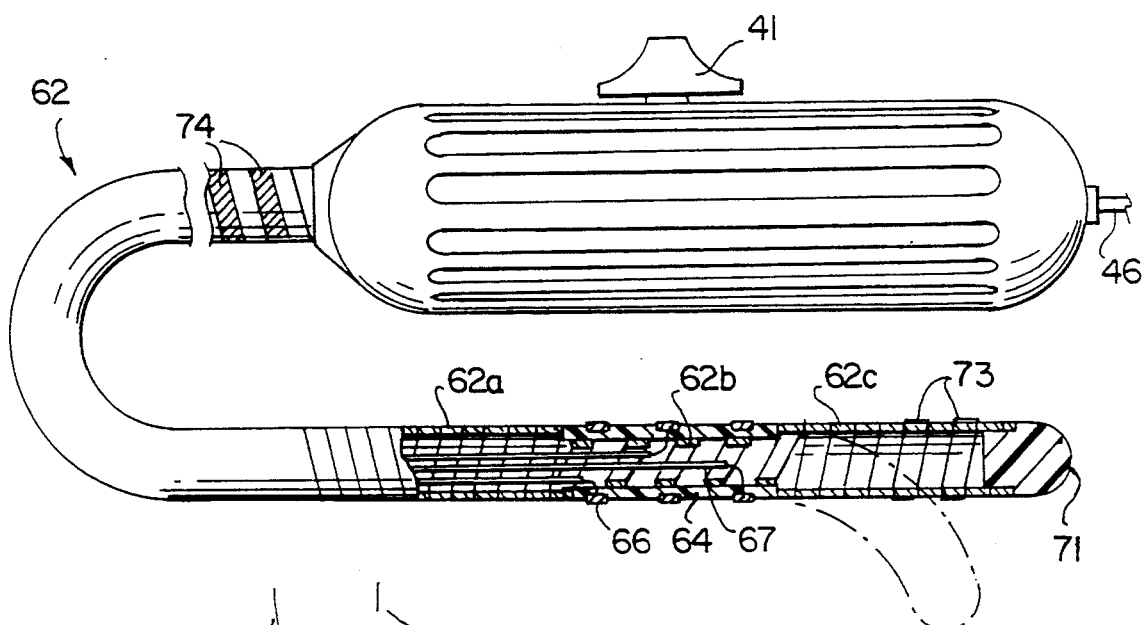
FIG. 5 is a side elevational view partially in cross section of the catheter shown in FIG. 4.

In general, the catheter assembly of the present invention for performing a medical procedure on a body consists of an introducer adapted to be inserted into a vessel of the patient. The introducer is provided with a plurality of lumens extending therethrough and opening into an entrance port. A plurality of catheters having proximal and distal extremities are removably positioned within the plurality of lumens in the introducer and extend distally of the introducer and are adapted to have their distal extremities positioned in different locations within the patient.

More in particular, as shown in the drawings, the catheter assembly 11 comprises a multi-port introducer 12 and a plurality of catheters 13 which are introduced through the multi-port introducer 12. The catheter assembly 11 is shown being utilized in FIG. 1 in connection with diagnostic procedures, as for example electrophysiology studies of the heart 16 of a patient 17 introduced through a femoral vein 18 of the patient.

The multi-port introducer 12 as shown in FIG. 2 consists of an introducer body 21 having proximal and distal extremities 22 and 23. The body 21 is formed of a suitable material such as a medical grade plastic and can be relatively flexible. The introducer 12 can be of a suitable size, as for example 6 or 7 French ranging from 0.080 to 0.093 inches in diameter. The distal extremity 23 is provided with a rounded slightly tapered end 24 to provide an atraumatic tip for the introducer 12. The proximal extremity 22 is enlarged and is provided with a plurality of ports 26 spaced circumferentially around an end wall 27, as for example four or more ports. The ports 26 open into lumens 28 which extend longitudinally of the body 21 and which open through openings 29 in the rounded tapered end 24. Because of the tapering of the end 24, the openings 29 have generally an oval-shaped configuration even though the lumens 28 are circular in cross section. The lumens 28 can have a suitable size which can accommodate the catheters 13 which are to be inserted therethrough. Thus, by way of example if the catheters are of a 2 French size, the lumens 28 should have a slightly greater size so that they can be introduced through the lumens with relatively little friction.

As shown in FIG. 2, a plurality of tubular members 31 are bonded to the proximal extremity 22 of the body 21 and are in registration with the ports 26 so that the ports 26 are in communication with the tubular members 31. Hemostatic valves 32 of a conventional type are mounted on and carried by the tubular members 31. They are sized so that they can accommodate the 2 French catheters 13 and form a seal therewith when the 2 French catheters are introduced through the introducer 12 as hereinafter described. It should be appreciated that if desired, hemostatic valves 32 can be incorporated in the proximal extremity 22 of the introducer body 21 and the tubular members 31 eliminated.

A catheter 13 utilized in the multi-port introducer 12 is shown in FIG. 4 and as shown therein consists of a flexible elongate member 36 which is provided with proximal and distal extremities 37 and 38. A handle 39 is secured to the proximal extremity 37 and includes a slider 41 which is slidably mounted in a slot 42 provided in the handle. The slider 41 controls means utilized for causing bending of the distal extremity 38. The handle is connected to first and second electrical cords 46 and 47 which are connected to plugs 48 and 49 that are utilized for a purpose hereinafter described. The distal extremity 38 can be bent in a conventional manner by the use of steering wires actuated by the slider 41 or alternatively by electrically energized Nitinol elements as described in U.S. Pat. No. 5,238,005, issued Aug. 24, 1993.

The flexible elongate member 36 is comprised of a tubular member 61 formed of a suitable material such as stainless steel and having a suitable diameter, as for example 2 French of approximately 0.026 inches in diameter.

It is desirable that the distal extremity 38 be very flexible and for that reason it is formed of a helical coil 62 which is flexible and hollow. The coil 62 can be formed of a suitable material such as a flat metal ribbon. Also, if desired, it can be formed of a radiopaque material such as tungsten platinum alloy or palladium.

The coil 62 can have a suitable length, as for example 20–30 centimeters and can be formed of flattened round wire as shown. At the very distal extremity of the coil, the coil 62 is provided with an initial portion 62a having approximately the same diameter of the tubular member 61 for a length from 10–20 centimeters which is followed distally by step down portion 62b of a smaller diameter which can be accomplished by utilizing a mandrel having the two different diameters with the portion 62b having suitable length, as for example 1–2 centimeters.

A tube 64 formed of a suitable insulating material, as for example shrink tubing formed of plastic is placed over the portion 62b. A plurality of electrodes 66 formed of a suitable material such as platinum are provided in longitudinally spaced-apart positions on the tube 64. The electrodes 66 are connected by insulated conductors 67 that extend interiorly of the coil 62 to the proximal extremity of the flexible elongate member 36 and are connected through the handle 39 to the cord 47 and the connector 49.

The last 5–10 millimeter portion 62a of the distal extremity of the coil 62 is of a larger diameter, as for example the same diameter as the portion 62a. In order to impart greater flexibility to this portion 62c, the coils are spaced-apart with each coil having a diameter ranging from 0.016 to 0.018 inches a thickness of 0.002 to 0.003 inches and a spacing therebetween ranging from 0.004 to 0.006 inches.

A rounded tip 71 is provided in the distal extremity of the portion 62c and is formed of a suitable material such as a platinum tungsten alloy or palladium. A marker 73 is carried by the distal extremity of the catheter 13 to identify the catheter. Such identifying markers 73 can be formed as a bond as shown of a suitable radiopaque material such as a tungsten platinum alloy or palladium. Thus, by way of example if four of the catheters 13 are to be utilized in connection with the introducer 12, the catheters can be coded or marked in such a manner that each is provided with the same marking on the proximal and distal extremities. Thus, for example two bands 73 can be provided on the distal extremity and similarly two markers 74 visible to the human eye such as colored markers can be provided on the proximal extremity.

In connection with the present invention, the two French catheters 13 can be designed to have the same mechanical characteristics, as for example a conventional 6 or 7 French size catheter. Thus the tubular member 61 can be formed in such a manner so as to provide good torquability characteristics whereby when the proximal extremity 37 is rotated, the distal extremity will rotate in a one-for-one relationship. The tubular member 61 can be formed in a conventional manner to achieve the desired stiffness and torque transfer capabilities desired. Preformed bends can be placed in the distal extremity 38 of the flexible elongate member 36 by forming the catheter 13 in a suitable manner. For example, the catheter 13 can be provided in a desired preformed shape which is assumed as soon as there is space for the distal extremity 38 to curve, as for example, as shown in broken lines in FIG. 4.

Conventional alternative steering means can be provided in which pull wires (not shown) are utilized controlled by actuation of the slider 41 or other appropriate mechanism. Similarly, Nitinol elements can be mounted in the distal extremity and can be electrically actuated by the slider 41 to accomplish the desired bending.

Operation and use of the catheter assembly 11 may now be briefly described as follows. Let it be assumed that the patient has been prepared for an electrophysiology study of the heart. The physician then makes the venous puncture in the femoral vein 18 of the patient. The introducer 12 is then introduced into the vein and the sutures as needed are placed around the puncture to prevent blood from leaking through the puncture. The hemostasis valves 32 provided in the multi-port introducer 12 are in a normally closed position to prevent blood from flowing therethrough. Catheters 13 are then introduced one by one through appropriate ports 26 through the hemostasis valves 32 to pass through the lumens 28 into the venous vessel 18 and then are advanced into appropriate locations in the venous side of the heart. As explained previously, this can be accomplished by utilizing catheters having preformed bends in the distal extremities or by steering the distal extremities utilizing the slider 41 on the handle 49 to either control the distal extremity by tensioning the pull wires or alternatively to supply energy to Nitinol elements disposed in the distal extremity. This latter approach is shown schematically in FIG. 1 in which a controller and power supply 76 is provided for each of the catheters 13. This controller and power supply can be provided in the handle 39 and be controlled by the slider 41. The signal outputs which are being measured by the electrodes 66 carried by the distal extremity of the catheters 13 can be viewed on instrumentation 78 connected to the connectors 48 connected to the handle 39 of each of the catheters 13.

During medical procedures, as for example an EP study, the physician can view the distal extremities of the catheters 13 by viewing the same under fluoroscopy and then can move the proximal extremities by movement of the handles. By observing the markings on the distal extremities of the catheters, the physician can associate a marking with a marking provided on the proximal extremity so that he can move the catheter he desires to move. Thus, the physician can advance or retract the distal extremity of the catheter by grasping on the handle 39. Also the physician can rotate the catheter by rotation of the handle 39. Bending can be accomplished by moving of the slider 41 on the handle 39.

After the medical procedure has been accomplished, as for example, the EP study has been completed, the catheters 13 can be removed one by one from the multi-port introducer 12 after which the multi-port introducer can be removed. Alternatively, the multi-port introducer 12 and the catheters 13 carried thereby can be removed as a unit. After the multi-port introducer 12 has been removed, the incision through which the introducer has been introduced can be closed in a conventional manner. It can be seen that with the catheter assembly 11 of the present invention and the method herein disclosed it is only necessary to make a single incision at a single site, into the patient while permitting multiple catheters to be introduced into the patient from this same site. This greatly decreases bleeding which may occur and minimizes the possibilities of the occurrence of hematomas.

Figure 6:
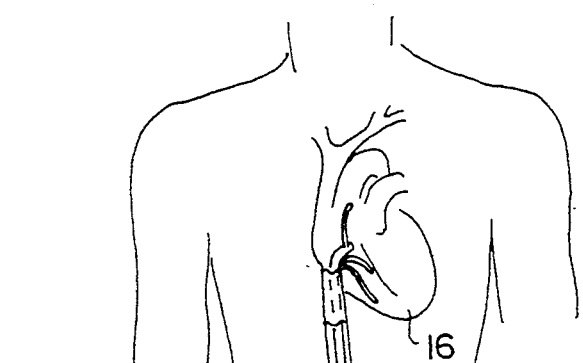
FIG. 6 is a schematic illustration showing a catheter assembly in which a longer multi-port introducer is utilized.
Figure 7:
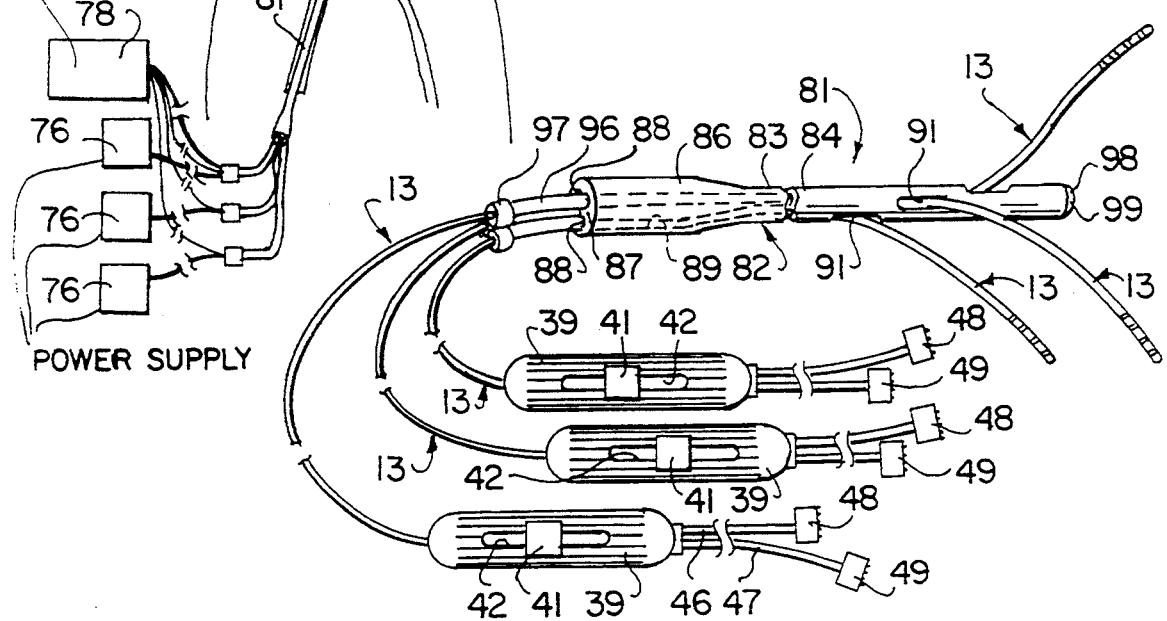
FIG. 7 is a side elevational view of the multi-port introducer shown in FIG. 6 with a plurality of catheters disposed therein.

In certain medical procedures utilized in the present invention may be desirable to provide a long multi-port introducer 81 which as shown schematically in FIG. 6 can again be introduced through the femoral vein 18 with the introducer having a length so that its distal extremity can be positioned near the opening to the right atrium of the heart at the junction of the superior and inferior vena cavas. A side elevational view of the long multi-port introducer 81 is shown in FIG. 7 with a plurality of catheters 13 of the type hereinbefore described disposed therein. The introducer 81 is provided with a body 82 generally of the same diameter as the body 21 of the multi-port introducer 12 and can have a suitable size, as for example 6–7 French. It is provided with proximal and distal extremities 83 and 84 and can have a suitable length, as for example 30–70 centimeters. The body 82 can be formed of a suitable material such as plastic. It is provided within a large head 86 formed integral with the proximal extremity 83 and is provided with a wall 87 having a plurality of spaced-apart ports 88 therein which open into lumens 89 that are in communication with staggered openings 91 provided in the distal extremity 84. The ports 88, the lumens 89 and the openings 91 are sized so that they can accommodate the catheters 13. Thus, by way of example if the catheters 13 are of the 2 French size the ports 88, the lumens 89 and the openings 91 should be of a size which is slightly greater than that to permit easy slidable movement of the catheters 13 within the introducer 81. Tubular members 96 are connected into the ports 88 and are provided with hemostatic valves 97 on their proximal extremities which are adapted to receive the catheters 13.

The openings 91 have been staggered on the distal extremity 84 to reduce the possibility of stasis in the blood which could potentially cause emboli. The distal extremity 84 has been provided with an atraumatic tip 98 similar to that hereinbefore described for the introducer 12. Thus, it can be seen that the openings 91 are positioned proximally of the tip 98 rather than having the openings be in the tip 24 as with the introducer 12 hereinbefore described. With a short introducer 12, it is more difficult to place the openings in the side of the introducer because there is a tendency for a catheter when it leaves the openings to turn on its axis making it difficult to form a sharp bend in the catheter. With the long introducer 81, this is less of a problem because the tip 93 can be positioned so that the catheters 13 can be readily positioned. A radiopaque material 99 can be provided on the tip 98 so that the tip can be visualized fluoroscopically.

Operation and use of the long introducer 81 in connection with the catheters 13 is similar to that hereinbefore described with the principal difference being that the long multi-port introducer 81 is positioned so that its tip is near the opening of the right atrium of the heart as hereinbefore described. Thereafter, the catheters 13 can be deployed and manipulated in the same manner as hereinbefore described to accomplish the desired medical procedures. After the desired medical procedure, as for example, an electrophysiology study has been completed, the catheters 13 can be removed after which the introducer 81 can be removed and the puncture site closed in a conventional manner.

From the foregoing it can be seen that with the catheter assembly of the type hereinbefore described utilizing either a short or a long multi-port introducer it is possible to utilize a plurality of small diameter catheters in the same introducer through a single puncture site thereby greatly reducing the number of puncture sites normally needed for performing certain medical procedures, as for example EP studies. Although the present method has been described principally in connection with conducting electrophysiology studies it can be seen that the concept of having a multi-port introducer with a plurality of small diameter tools, as for example catheters introduced through the multi-port introducer, other medical procedures can be performed where multiple instruments or tools are required. It also should be appreciated that although the method has been described particularly for use in the venous side of the heart, similar studies and procedures can be accomplished on the arterial side of the heart. It also should be appreciated that in addition to introduction through the femoral veins and arteries, other vessels of the patient can be utilized, as for example jugular veins and arteries. Also, one of the ports in the introducer may be utilized, if needed, for saline drip/or heparin drip. This further eliminates the necessity of one additional puncture site.

What is claimed is:

1. A catheter assembly for use in performing a medical procedure within a region in the body of a patient having a vessel therein comprising a multi-port introducer adapted to be inserted into a vessel of the patient, the multi-port introducer comprising a body having proximal and distal extremities and having at least three separate spaced-apart lumens therein extending from the proximal extremity to the distal extremity, said body having ports therein at the proximal extremity in communication with the lumens and openings at the distal extremity in communication with the lumens, the body having a length so that it can extend from the exterior of the body to said region in the body and a plurality of catheters, each of said catheters being slidably disposed in a separate lumen in the multi-port introducer and being adapted to be disposed in the vessel of the patient.

2. A catheter assembly for use in performing a medical procedure in the body of a patient having a vessel therein comprising a multi-port introducer adapted to be inserted into a vessel of the patient, and a plurality of catheters disposed in the multi-port introducer and adapted to be disposed in the vessel of the patient, said multi-port introducer having a size ranging from 6-7 French and said catheters having a size of approximately 2 French.

3. An assembly as in claim 2 wherein said multi-port introducer has a length ranging from 6-7 centimeters.

4. A catheter assembly as in claim 2 wherein said introducer has a length ranging from 30-50 centimeters.

5. A catheter assembly as in claim 2 wherein said introducer has an atraumatic tip.

6. A multi-port introducer for use in performing a medical procedure within a region of the body of a patient with a plurality of catheters to be used in conjunction therewith comprising a body having proximal and distal extremities, the body having a length so that it can extend from the exterior of the body to the region within the body, a plurality of separate spaced-apart lumens disposed in the body and extending from the proximal extremity to the distal extremity, said body having ports therein in the proximal extremity in communication with the lumens and having openings in the distal extremity in communication with the lumens, said ports, said lumens and said openings being sized whereby a plurality of individual catheters can be introduced into and retained at the same time in the region of the body through the separate, spaced-apart lumens in the multi-port introducer.

7. An introducer as in claim 6 wherein said proximal extremity is provided with an atraumatic tip.

8. An introducer as in claim 6 wherein said openings are disposed in said atraumatic tip.

9. An introducer as in claim 6 wherein said openings are staggered proximally of the atraumatic tip.

10. An introducer as in claim 6 wherein said body has a size ranging from 6-7 French and wherein said lumens have a size of approximately 2 French.

11. An introducer as in claim 6 together with tubular members in communication with the ports and hemostatic valves carried by the tubular members.

12. A combination for use in performing a medical procedure in the body, at least two catheters to be utilized at the same time during the medical procedure, each catheter comprising a flexible elongate member having proximal and distal extremities, a handle secured to the proximal extremity and corresponding markers carried by the proximal and distal extremities which differ visually from the other of at least two catheters so that one catheter of at least two catheters can be distinguished visually from another of at least two catheters while the distal extremities of at least two catheters are disclosed within the body.

13. A catheter as in claim 12 wherein said marker on said distal extremity is formed of a radiopaque material and wherein said marker on the proximal extremity is visible to the human eye.

14. A kit for performing medical procedures within a region of the body, a multi-port introducer disposed in the kit and a plurality of catheters disposed in the kit and adapted to be introduced through the multi-port introducer, each of the catheters having proximal and distal extremities and being provided with corresponding markings on the proximal and distal extremities which differ visually from corresponding markings of the other of the plurality of catheters whereby the catheters can be distinguished visually from one another by the markings when the distal extremities of the plurality of catheters are disposed at the same time in the region of the body.

15. A method for performing a medical procedure within a region of the patient having a vessel by the use of a multi-port introducer having proximal and distal extremities with spaced apart separate lumens extending from the proximal extremity to the distal extremity with separate ports in the proximal extremity and separate openings in the distal extremity in communication with the lumens and a plurality of catheters adapted to be inserted through the multi-port introducer and having proximal and distal extremities comprising forming a single puncture site in the patient leading to the vessel, introducing the multi-port introducer through the puncture site into the vessel, introducing the plurality of catheters through the ports in the multi-port introducer so that each enters a separate port, advancing the catheters in the lumens so that each catheter is advanced through a separate lumen and exits through a separate opening into the vessel so that the distal extremities of the plurality of catheters are disposed in the vessel at the same time and performing medical procedures with the plurality of catheters in the patient, removing the catheters, removing the multi-port introducer and closing the single puncture site.

16. A method as in claim 15 wherein the catheters are marked on the proximal and distal extremities so that the catheters can be visually distinguished one from another while the distal extremities are disclosed in the vessel together with the step of moving the catheters individually in accordance with the markings carried thereby to position the distal extremities of the same in the vessel of the patient.

* * * * *

UNITED STATES PATENT AND TRADEMARK OFFICE
CERTIFICATE OF CORRECTION

PATENT NO. : 5,342,295
DATED : August 30, 1994
INVENTOR(S) : Mir A. Imran

It is certified that error appears in the above-indentified patent and that said Letters Patent is hereby corrected as shown below:

Column 8, line 6, Claim 12, delete "disclosed" and insert therefor --disposed--.

Signed and Sealed this

Twenty-seventh Day of February, 1996

Attest:

BRUCE LEHMAN

Attesting Officer     Commissioner of Patents and Trademarks